US007611505B2

(12) United States Patent
Ranalletta et al.

(10) Patent No.: US 7,611,505 B2
(45) Date of Patent: Nov. 3, 2009

(54) STERILE DOCKING APPARATUS AND METHOD

(75) Inventors: Joseph V. Ranalletta, Englewood, CO (US); Robert S. Brereton, Centennial, CO (US)

(73) Assignee: Baxa Corporation, Englewood, CO (US)

( * ) Notice: Subject to any disclaimer, the term of this patent is extended or adjusted under 35 U.S.C. 154(b) by 769 days.

(21) Appl. No.: 11/125,774

(22) Filed: May 10, 2005

(65) Prior Publication Data
US 2006/0259013 A1 Nov. 16, 2006

(51) Int. Cl.
*A61M 25/00* (2006.01)
(52) U.S. Cl. ...................... 604/539; 604/533
(58) Field of Classification Search ............. 604/513, 604/533, 539; 114/44; 340/958; 710/303
See application file for complete search history.

(56) References Cited

U.S. PATENT DOCUMENTS

| 4,411,656 | A | | 10/1983 | Cornett, III | 604/212 |
|---|---|---|---|---|---|
| 4,425,113 | A | | 1/1984 | Bilstad | |
| 4,534,573 | A | | 8/1985 | Somers | 279/149 |
| 4,597,758 | A | | 7/1986 | Aalto et al. | 604/156 |
| 4,821,996 | A | | 4/1989 | Bellotti et al. | |
| 5,265,822 | A | | 11/1993 | Shober, Jr. et al. | 242/388.2 |
| 5,354,275 | A | * | 10/1994 | Behnke et al. | 604/86 |
| 5,402,982 | A | * | 4/1995 | Atkinson et al. | 251/149.1 |
| 5,535,785 | A | | 7/1996 | Werge et al. | 137/843 |
| 5,620,427 | A | | 4/1997 | Werschmidt et al. | 137/843 |
| 5,676,346 | A | | 10/1997 | Leinsing | 251/149.1 |
| 5,681,279 | A | | 10/1997 | Roper et al. | 604/57 |
| 5,699,821 | A | | 12/1997 | Paradis | 137/1 |
| 5,702,374 | A | | 12/1997 | Johnson | 604/283 |
| 5,730,723 | A | | 3/1998 | Castellano et al. | 604/68 |

(Continued)

FOREIGN PATENT DOCUMENTS

EP 0716860 6/1996

(Continued)

OTHER PUBLICATIONS

White Paper/Feb. 2002 by KippGroup, Comparison of Contamination Rates among Needless Access Devices in Simulated Clinical Use, 4 pages.

(Continued)

*Primary Examiner*—Nicholas D Lucchesi
*Assistant Examiner*—Gerald Landry, II
(74) *Attorney, Agent, or Firm*—Marsh Fischmann & Breyfogle LLP

(57) ABSTRACT

An improved sterile docking apparatus for a medical-liquid, male connectors includes a holding member having an opening for matably receiving a nozzle end of a medical-liquid, male connector therethrough, and a film member disposed across the opening, wherein the film member is stretchable to envelope and thereby isolate a nozzle end of a medical-liquid, male connector that is inserted into the opening of the holding member. The film member may be elastic, wherein it substantially returns to an initial configuration after removal of a nozzle end of a medical-liquid, male connector from the opening of the holding member. An interconnection surface may be provided on the holding member of the docking apparatus to interface with a complimentary interconnection surface of a medical-liquid, male connector so as to maintain the nozzle end of the medical-liquid, male connector in an enveloped position during docking.

27 Claims, 8 Drawing Sheets

U.S. PATENT DOCUMENTS

| | | | | |
|---|---|---|---|---|
| 5,775,671 | A * | 7/1998 | Cote, Sr. | 251/149.8 |
| 5,782,816 | A | 7/1998 | Werschmidt et al. | 604/256 |
| 5,788,215 | A | 8/1998 | Ryan | 251/149.6 |
| 5,807,345 | A | 9/1998 | Grabenkort | 604/256 |
| 5,814,024 | A * | 9/1998 | Thompson et al. | 604/246 |
| 5,820,602 | A | 10/1998 | Kovelman et al. | 604/187 |
| 5,851,201 | A | 12/1998 | Ritger et al. | 604/240 |
| 5,855,230 | A | 1/1999 | Guala et al. | 138/89 |
| 5,947,954 | A | 9/1999 | Bonaldo | 604/533 |
| 5,954,313 | A | 9/1999 | Ryan | 251/149.1 |
| 5,984,373 | A | 11/1999 | Fitoussi et al. | 285/92 |
| 6,032,926 | A * | 3/2000 | Fuchs | 251/149.4 |
| 6,039,302 | A | 3/2000 | Cote, Sr. et al. | 251/149.1 |
| 6,063,062 | A | 5/2000 | Paradis | 604/249 |
| 6,152,913 | A | 11/2000 | Feith et al. | 604/533 |
| 6,158,458 | A | 12/2000 | Ryan | 137/515.5 |
| 6,171,287 | B1 | 1/2001 | Lynn et al. | 604/256 |
| 6,217,560 | B1 | 4/2001 | Ritger et al. | 604/243 |
| RE37,357 | E | 9/2001 | Lynn | 137/843 |
| 6,332,633 | B1 | 12/2001 | Fitoussi et al. | 285/332 |
| 6,394,983 | B1 | 5/2002 | Mayoral et al. | 604/192 |
| 7,081,982 | B2 * | 7/2006 | Shimazu et al. | 359/298 |

FOREIGN PATENT DOCUMENTS

WO     WO 0193936     12/2001

OTHER PUBLICATIONS

OPIT Source Book, Feb. 2001 Edition, by Abbott Laboratories, The LifeShield, Clave and Connector Family, www.optisourcebook.com, 5 pages.

Product Information Card by Baxter, Interlink IV Access Systems, 1 Page.

Information Page by Baxter, Interlink Needle-Less IV Access System, www.life-assist.com, 37 Pages.

Infusion Therapy, Lifeshield Prepierced Reseal and Blunt Cannula System, 2002, Edition, by Abbott Laboratories, www.abbotthosp.com, 11 Pages.

Syringe Infusion/Syringe Infuser Accessories, Baxa Product Catalog, by Baxa Corporation, www.baxa.com, 2 Pages.

\* cited by examiner

STERILE DOCKING APPARATUS AND METHOD

FIELD OF THE INVENTION

The present invention relates to the field of medical liquid administration, and more particularly, to an improved docking apparatus and method for enhancing the maintenance of sterility of a nozzle end of a male connector fluidly interconnected or interconnectable to a medical liquid source during one or repeated periods of non-use (e.g. between successive administrations of a medical liquid through a vascular catheter over an extended time period).

BACKGROUND OF THE INVENTION

Numerous techniques are employed for the administration of "medical liquids" (e.g. liquid medication and flush solutions) to a patient. In particular, where repeated medication infusions are required, medical liquids are often administered via the use of a vascular access catheter that is fluidly interconnected or interconnectable to one or more medical liquid sources via an associated tubing line set. Typically, the catheter is inserted into the vein of a patient and left there for multiple intravenous (IV) infusions during an extended course of medication therapy. By way of example, the time period between IV drug infusions may be between about 4 to 24 hours, wherein the IV liquid medication source is typically replaced after each dose infusion.

In conjunction with extended therapy applications, a desirable practice is to disconnect a vascular catheter from a medical liquid source(s) between infusions. In this regard, most patients receiving IV medication therapy are ambulatory to some degree and benefit from not being continuously connected to a medical liquid source(s).

To facilitate the ready and repeated connection/disconnection of a vascular catheter and medical liquid source(s), while avoiding the use of needle-type arrangements (e.g. arrangements where sharp/blunt needle ends are inserted into specialized vascular catheter connection ports having a piercable/slit stopper), complimentary female and male connectors are often utilized (e.g. male and female luer connectors). For purposes hereof, a "male connector" generally refers to any fluid connector having a nozzle end that projects into a "female connector" upon interconnection therewith, wherein fluid transfer between the male and female connector may be realized. In this regard, for example, a female connector may be fluidly interconnected as an access port to the vascular catheter and a complimentary male connector may be fluidly interconnected or readily interconnectable to a medical liquid source(s).

In order to maintain sterility, the medical-liquid, male connector is typically covered with a new cap after each disconnection from the female connector, and a depressible member of the medical-liquid, female connector is contacted with an antibacterial material (e.g. an alcohol solution) before each interconnection with the male connector. Such an approach entails the unpackaging, use and disposal of multiple caps over an extended medication therapy. For example, where liquid medication is administered at least every four hours over a three-day period at least 18 caps would be required to maintain the sterility of the medical-liquid, male connector. As may be appreciated, cap-related costs, medical personnel time expenditures and inventory management implications associated with this approach can become quite significant.

SUMMARY OF THE INVENTION

In view of the foregoing, a broad objective of the present invention is to facilitate both the sterile and cost-effective handling of medical-liquid, male connectors that are interconnected/disconnected from complimentary female connectors more than once in the course of medical-liquid delivery, and particularly in applications where multiple vascular catheter connections/disconnections with a medical liquid source(s) are entailed in the course of IV medication therapy.

Further, a related objective of the present invention is to address the broad objective in a manner that reduces medical accessory costs, inventory management requirements and medical personnel time expenditures.

Another objective of the present invention is to provide for enhanced sterile handling of medical-liquid, male connectors during periods of non-use in a manner that is both convenient and space-efficient at a patient care site.

One or more of the above objectives and additional advantages are realized by the inventive docking apparatus and method disclosed herein. In particular, a dedicated apparatus is provided for docking a medical-liquid, male connector that is fluidly interconnected or connectable to a medical liquid source during one or repeated periods of non-use. The docking apparatus comprises a holding member having an opening for matably receiving a nozzle end of a medical-liquid, male connector therethrough, and a film member disposed across the opening. Of note, the film member is stretchable so as to isolate a nozzle end of a medical-liquid, male connector that engages the film member upon insertion through the opening of the holding member. That is, the film member is provided to stretch upon engagement by the nozzle end of a medical-liquid, male connector and thereby envelop the nozzle end in a tent-like manner so as to maintain the sterility of the nozzle end during docking use of the inventive apparatus.

In this regard, it is preferable for the film member to be capable of at least about 400% elongation, and more preferably at least about 700% elongation (e.g. elongation per unit length while maintaining at least a degree of elasticity sufficient to maintain contact between the film member and nozzle end of a male connector during docking use). Even more preferably, the film member may be elastic so that it is able to elastically deform during docking use and substantially return to its initial configuration after removal of a nozzle end of a medical-liquid, male connector from the holding member opening, thereby enhancing repeated docking use of the docking apparatus. More particularly, it is preferable that the film member be provided to have a modulus of elasticity of at least about 1000 psi, and even more preferably of at least about 3000 psi. By way of example, an elastic film member may comprise a polymer-based material, such as a material selected from a group comprising: thermoset rubbers and thermoplastic polyurethanes.

In certain arrangements, the stretchable film member may comprise an antimicrobial material. For example, the film member may comprise metal ions that provide an antibacterial effect (e.g. silver salts such as sulfadiazine).

In one aspect of the invention, the film member may be disposed to extend across an opening at one end of the holding member, thereby facilitating ready access to the film member for cleaning and contact with an antibacterial material prior to docking use. In one arrangement, the film member may be disposed over an opening at the top end of a tubular portion of the holding member. In another arrangement, the film member may be fixedly interconnected about the periphery of an opening of a ring-shaped portion of a holding member. In yet another arrangement, the film member may be disposed to extend across an opening of a tubular portion of the holding member in recessed relation to a top end of the tubular portion.

In another aspect of the invention, the film member may be provided to define a continuous, substantially planar or convex, outer surface portion across the opening at one end of the holding member prior to insertion of a nozzle end of a medical-liquid, male connector. As may be appreciated, the provision of such an outer surface portion on the film member further facilitates cleaning and the application of an anti-bacterial material thereto prior to engagement with the nozzle end of a medical-liquid, male connector. Additionally, such outer surface portion facilitates contact engagement across an entire distal edge of a nozzle end of a medical-liquid, male connector during docking use.

In another aspect of the present invention, an interconnection surface may be provided on the holding member (e.g. on an outside or inside surface of a tubular portion of the holding member), wherein the interconnection surface is adapted for selective interconnection/disconnection with a complimentary interconnection surface a medical-liquid, male connector. As may be appreciated, in some arrangements the complimentary interconnection surface may be the same means that is utilized for fluidly interconnecting the medical-liquid, male connector to a patient (e.g. via a vascular catheter interface for medical-liquid administration).

In one approach, the interconnection surface may comprise a threaded surface provided on an outside surface or on an inside surface of a tubular portion of the holding member that is sized/shaped to threadably interface with a complimentary threaded surface provided on an inside surface of a collar or on an outside surface of a nozzle end, respectively, of a medical-liquid, male connector. For example, an outside surface of a tubular portion of the holding member may be threaded to interface with an internally threaded, rotatable collar of a medical liquid, male luer connector that is utilized for selective interconnection/disconnection from a female connector fluidly interconnected with a vascular catheter.

In another approach, the interconnection surfaces on the docking apparatus and medical-liquid male connector may comprise one or more projections that are sized/shaped to allow for relative passage past each other upon linear advancement and then to interfere upon relative rotation so as to maintain the medical liquid, male connector in a docked position. In yet another approach, one or both of the interconnection surfaces on the docking apparatus and medical-liquid, male connector may be tapered to facilitate a friction-fit interface therebetween. For example, the interconnection surface of the docking apparatus may define the periphery of the holding member opening and be of a size/shape to slidably receive a tapered nozzle end of a medical-liquid, male connector that is of complimentary size/shape to yield a friction-fit interface.

In a further aspect of the invention, the film member may be disposed relative to an interconnection surface on the docking apparatus so that the film member is interposed in contact engagement between such interconnection surface and a complimentary interconnection surface of a medical-liquid male connector during docking use. As such, an antibacterial material applied to an outer surface of the film member may contact the complimentary interconnection surface during docking. In turn, the maintenance of sterility of a complimentary interconnection surface of a medical-liquid, male connector may be enhanced.

In yet another aspect, the film member may be provided to extend over and laterally and outwardly away from an opening at one end of the holding member. In turn, the film member may be interconnected to the docking apparatus about a ring, wherein an operative area is defined within the ring that is greater than the area of the opening. In certain arrangements, the film member may stretch across such operative area during docking use. That is, in such arrangements the film member may advantageously stretch across an area larger than the holding member opening during a first stage of docking (e.g. until the film member is restrainably engaged between at least a portion of the interconnection surfaces of the docking apparatus and a medical-liquid, male connector), wherein further stretching during a second stage of docking is substantially limited to a smaller area of the film member. To facilitate stretching of the film member across a surface area larger than the opening of the holding member, an interconnection surface may be provided on the holding member that yields a predetermined clearance relative to a complimentary interconnection surface of a medical-liquid, male connector. For example, in arrangements where a threaded interconnection surface is provided on the outside of a tubular portion of the holding member, it may be preferable to provide a clearance between such interconnection surface and a complimentary internally threaded surface of a collar of a medical-liquid, male connector of at least 2 times and most preferably between about 2 to 4 times the thickness of the film member. Further, in such arrangements it may be preferable to provide a holding member opening whose periphery provides a predetermined clearance relative to a docked nozzle end of a medical-liquid, male connector of at least 2 times the material thickness of the film member.

In one embodiment, the film member may extend across and angle downwardly and away from a top end of a tubular portion of the holding member to define a continuous, outer surface that includes a continuous, substantially planar or convex, outer surface portion and a surrounding (e.g. ring-shaped), conical, outer surface portion. When an interconnection surface is provided on an outside surface of a tubular portion of the holding member, the conical, outer surface portion of the film member may be provided to extend over and about the interconnection surface, wherein the film member is interposed in contact engagement with and between the interconnection surface of the holding member and a complimentary interconnection surface on the inside of a collar of a medical-liquid, male connector during docking use of the docking apparatus. As may be appreciated, such an arrangement facilitates the application of an anti-bacterial material to the outer surface of the film member and contact engagement thereof with an interconnection surface of a medical-liquid, male connector (e.g. internal threads of a collar) during docking use.

In another embodiment, the docking apparatus may further include a flange member interconnected to the holding member and extending laterally away from a tubular portion of the holding member, wherein at least a portion of the tubular portion of the holding member and at least a portion of a conical, outer surface portion of the film member each at least partially project through an aperture that is provided through the flange member. In turn, an interconnection surface may be provided on the outside surface of the tubular portion to interface with a complimentary interconnection surface of a collar of a medical-liquid, male connector. In such embodiments, it is preferable for the aperture to be sized to receive a range of outside collar widths utilized on medical-liquid, male connectors, including male luer type connectors.

In certain embodiments the holding member may include a laterally-extending portion that extends away from a tubular portion thereof, wherein the laterally-extending portion and a flange member may be adapted for ready interconnection with a peripheral ring portion of the film member captured therebetween. By way of example, a plurality of clip extensions may be provided about a periphery of the flange member for snap-on interconnection of the flange member to a laterally-extending portion of the holding member. As may be appreciated, the inclusion of a flange member and/or a laterally-extending portion of a holding member also facilitates grasping and manipulation of the docking apparatus by a user.

Additional user-friendly features may be included in the inventive docking apparatus. For example, an outer surface portion of the film member may be provided in coaxial alignment with the holding member opening and may be presented in a visually distinct manner to facilitate insertion of a nozzle end of a medical-liquid, male connector into the opening. In this regard, such outer surface portion of the film member may be provided to correspond in shape with the opening of a holding member, In one approach, a substantially planar or convex, outer surface portion of the film member, and a surrounding (e.g. ring-shaped), conical, outer surface portion of the film member, may be provided to be visually distinct to a user. Similarly, a top surface of the flange member may be presented to be visually distinct from one or both of the noted surface portions of the film member.

As may be appreciated, an inventive method for docking a medical-liquid, male connector is also provided. The inventive method includes the steps of engaging a nozzle end of a medical-liquid, male connector with an outer surface of a film member disposed across an opening of a holding member of a docking apparatus (i.e. by advancing at least one of the medical-liquid, male connector and docking apparatus toward the other), and stretching the film member of the docking apparatus to envelop the nozzle end of the medical-liquid, male connector (i.e. by further relative advancement as the nozzle end is inserted through the opening of the holding member of the docking apparatus). In turn, sterility maintenance of the nozzle end of the medical-liquid, male connector is enhanced during docking.

The inventive method may further comprise the step of contacting the outer surface of the film member of the docking apparatus with an anti-bacterial material prior to the engaging and stretching steps. By way of example, the contacting step may entail passing a swab across the outer surface of the film member, wherein the swab comprises or has otherwise been contacted with an anti-bacterial material.

In one aspect, the inventive method may further include the step of interconnecting the medical-liquid, male connector with the docking apparatus (e.g. in conjunction with or after said stretching step), wherein the nozzle end of the medical-liquid, male connector is maintained in the enveloped position. In relation to the interconnecting step, a distal edge of the nozzle end of the medical-liquid, male connector may be maintained in contact engagement with the outer surface of the film member of the docking apparatus (i.e. throughout the interconnecting step). In this manner, the maintenance of sterility is further enhanced.

The interconnecting step may include the substep of interfacing an interconnection surface on the holding member of the docking apparatus in retentive relation with a complimentary interconnection surface of the medical-liquid, male connector. In one approach, the complimentary interconnection surface on the medical-liquid, male connector may be provided on a rotatable collar thereof, and the interfacing step may entail rotatably advancing the collar of the medical-liquid, male connector relative to the holding member of the docking apparatus (e.g. so as to threadably engage compatible threaded surfaces comprising the respective interconnection surfaces).

In another aspect of the inventive method, the film member of the docking apparatus may be interposed between and in contact relation with both of the interconnection surfaces of the holding member of the docking apparatus and the medical-liquid, male connector throughout the above-noted interconnecting step. In this manner, sterility may also be further enhanced.

In another aspect, the stretching step of the inventive method may comprise first and second stages. In the first stage, the film member may be stretched across an area that is larger than the area of the opening of the holding member of the docking apparatus. By way of example, this may be achieved by disposing the film member to extend over and laterally away from one end of the holding member as noted above. In a second stage of the stretching step, the film member is restrainably interposed between complimentary interconnection surfaces of the docking apparatus and medical-liquid, male connector, and therefore stretching of the film member is substantially limited to a smaller area than during the first stage. Providing a larger area for first stage stretching facilitates the maintenance of elastic deformation capabilities of the film member.

In yet a further aspect, the inventive method may include the additional steps of disconnecting the medical-liquid, male connector from the docking apparatus, and disengaging the nozzle end of the medical-liquid, male connector from the surface of the film member, wherein the surface of the film member substantially returns to an initial, pre-docking configuration (i.e. the configuration of the film member prior to the initial engaging step). As may be appreciated, the inventive method may further comprise the step of repeating the above-noted engaging, stretching, interconnecting, disconnecting, and disengaging steps a plurality of times. In this manner, it may be appreciated that the inventive method provides for the repeated use of a docking apparatus to maintain the sterility of one or more nozzle end(s) of medical-liquid, male connector(s) over an extended period of use.

Additional aspects and advantages of the present invention will be appreciated by those skilled in the art upon further consideration of the description that follows.

DETAILED DESCRIPTION OF THE INVENTION

Figure 3:
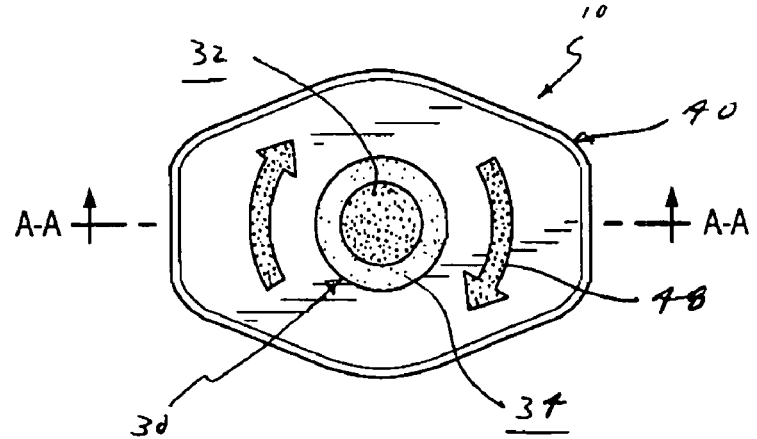
FIG. 3 is a top view of the docking apparatus embodiment of FIGS. 1 and 2.
Figure 4:
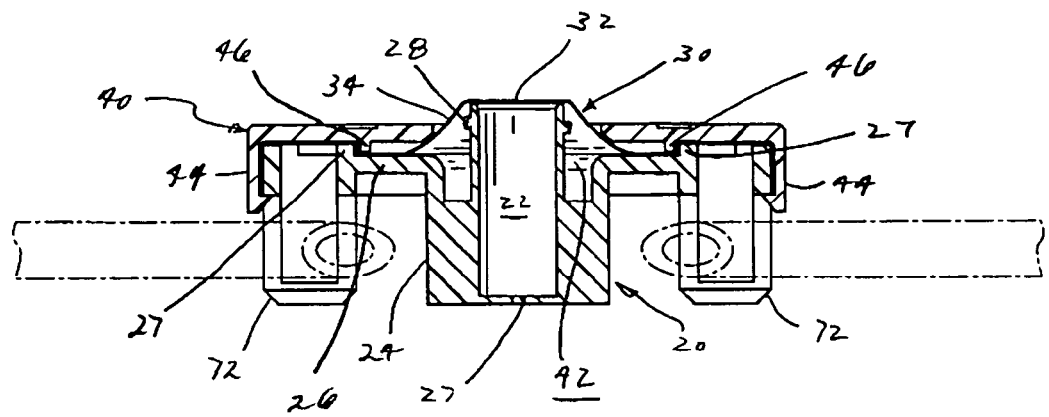
FIG. 4 is a side, cross-sectional view of the docking apparatus embodiment of FIGS. 1-3, taken along section line AA of FIG. 3.
Figure 5:
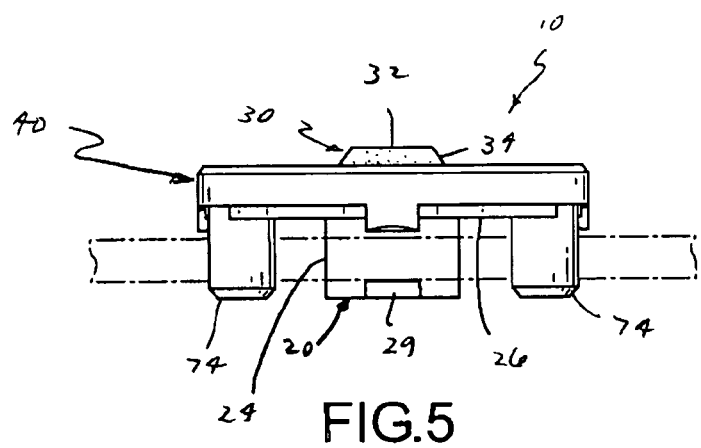
FIGS. 5 and 6 illustrate side and end views, respectively, of the docking apparatus embodiment of FIGS. 1-4.
Figure 6:
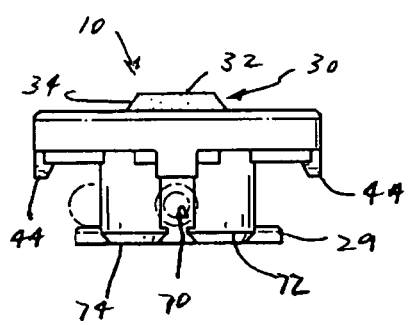

FIGS. 1-6 illustrate one embodiment of a medical-liquid, male connector docking apparatus 10 comprising the present invention. As best shown by FIG. 4, the docking apparatus 10 includes a holding member 20 having an opening 22 and a stretchable, sheet-like film member 30 disposed across the opening 22. The stretchable nature of film member 30 facilitates the isolation of a nozzle end of a medical-liquid, male connector that is inserted into the opening 22 by responsively stretching to envelop the nozzle end in a tent-like manner. By virtue of such isolation, maintenance of the sterility of a nozzle end of a medical-liquid, male connector may be enhanced.

Preferably the film member 30 is not only stretchable, but is also elastic, wherein the film member 30 is able to elastically deform during use and substantially return to its initial configuration after removal of a nozzle end of medical-liquid, male connector from opening 22. For example, film member 30 may comprise a polymer-based material such as the material selected from a group comprising: thermoset rubbers and thermoplastic polyurethanes.

In preferred arrangements, film member 30 may be of a substantially uniform thickness. By way of example, such thickness may be at least about 0.006 in., and preferably between about 0.006 in. and 0.009 in.

The film member 30 may be provided to define a continuous, substantially planar surface portion 32 that extends across and coincides with the shape of the opening 22, thereby facilitating the application of an anti-bacterial material thereto prior to being engaged by the distal edge of a nozzle end of a medical-liquid, male connector. In turn, contact engagement across the distal edge of a nozzle end of a medical-liquid, male connector is enhanced. To yield such an arrangement, film member 30 may extend over the opening 22 in co-planar relation to a periphery of the opening 22, as shown in FIG. 4.

Of further note, it may be desirable for the film member 30 to comprise an anti-bacterial material such as metal ions (e.g. silver salts such as sulfadiazine). As may be appreciated, the utilization of a film member 30 comprising an anti-bacterial material further enhances the maintenance of sterility upon contact engagement with a nozzle end of a medical, male connector.

The holding member 20 may include a tubular portion 24, wherein the opening 22 is located at a top end of the tubular portion 24. In the illustrated embodiment, the holding member 20 further comprises a laterally-extending portion 26 extending away from the tubular portion 24. Further, the docking apparatus 10 includes a flange member 40 extending away from the tubular portion 26 and interconnected to the laterally-extending portion 26 of the holding member 20. The provision of laterally-extending portion 26 and/or flange member 40 provides a structure that may be readily grasped by a user for use and manipulation of the docking apparatus 10.

The top end of the tubular portion 24 of the holding member 20 projects through and away from an aperture 42 provided through the flange member 40. Preferably the aperture 42 has a diameter of at least about 0.375 in., and even more preferably between about 0.4375 in. and 0.75 in.

The film member 30 is disposed over the top end of the tubular portion 24 of the holding member 20 and captured between the laterally-extending portion 26 of the holding member 20 and the flange member 40, wherein the film member 30 defines a continuous, frusto-conical, outer surface that also projects outward from the flange member 40. That is, the frusto-conical surface includes the above-noted planar surface portion 32, and a surrounding, ring-shaped, conical surface portion 34. As may be appreciated, the frusto-conical, outer surface may be readily contacted with a anti-bacterial material prior to the insertion of a nozzle end of a medical-liquid, a male connector through the opening 22 of the docking apparatus 10.

To provide for retentive engagement between the docking apparatus 10 and a medical-liquid, male connector, an interconnection surface 28 may be provided on the tubular portion 24 of holding member 20. More particularly, the interconnection surface 28 may be adapted to interface with a complimentary interconnection surface provided on a medical-liquid, male connector, wherein the film member 30 is interposed between the interconnection surface 28 of the docking apparatus 10 and the interconnection surface of a medical-liquid, male connector during docking use.

In the illustrated embodiment, interconnection surface 28 comprises a threaded surface on an outer surface of tubular portion 28 that may interface with a complimentary, threaded interconnection surface on the inside of a collar of a medical-liquid, male connector. In turn, the ring-shaped, conical surface 34 of film member 30 may be restrainably engaged between the two interconnection surfaces during docking. As shown, the frusto-conical surface of film member 30 is provided so as to extend over and about the interconnection surface 28 prior to docking use.

To accommodate stretching of the film member 30 during interconnection of the docking apparatus 10 with a medical-liquid, male connector, the threads of interconnection surface 28 in the illustrated embodiment may be rounded. Further, the distal end of the threads of interconnection surface 28 may be set back a distance from the distal end of the tubular portion 24

Additionally, it may be preferable to provide for a predetermined clearance between the threaded interconnection surface 28 and complimentary threaded interconnection surface of a medical-liquid, a male connector. In particular, a predetermined clearance of at least 2 times the thickness of film member 30 is preferred. In addition, it may be preferable for the periphery of opening 22 of a holding member 20 to provide a clearance relative to a docked nozzle end of a medical-liquid, male connector of at least 2 times the thickness of film member 30.

To facilitate the interconnection of the holding member 20 and flange member 40, flange member 40 may be provided with a plurality of clip extensions 44 about its periphery. Such clip extensions 44 are sized/shaped to extend around a peripheral edge of the laterally-extending portion 26 of the holding member 20 and retainably engage the underside thereof in a snap-on-like manner. In this regard, it may be appreciated that the assembly of docking apparatus 10 may be completed in a relatively simple manner.

For example, film member 30 may be sized/shaped slightly larger than the top aspect of holding member 20 and positioned over the holding member 20. Next, the flange member 40 may be advanced relative to the holding member 20 with the film member 30 captured therebetween. In this regard, the flange member 40 may be provided with an annular, downward-facing ring 44 that may be adjacently located within a concentric, upward-facing annular ring 27 provided on the laterally-extending portion 26 of the holding member 20, wherein the film member is secured therebetween about a ring-shaped region. As may be appreciated, the film member 30 is operative to stretch across the area that is within the ring-shaped region. Further, the film member may be slightly tensioned upon assembly.

Figure 1:
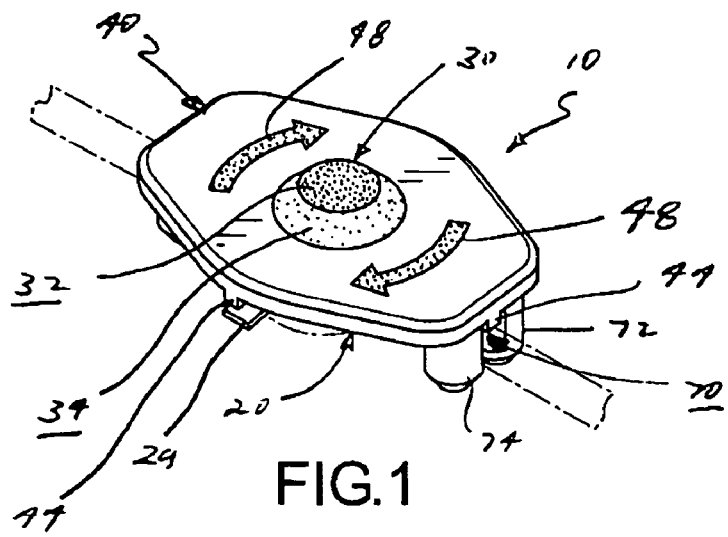
FIGS. 1 and 2 are perspective views of a top side and bottom side, respectively, of one docking apparatus embodiment of the present invention.
Figure 2:
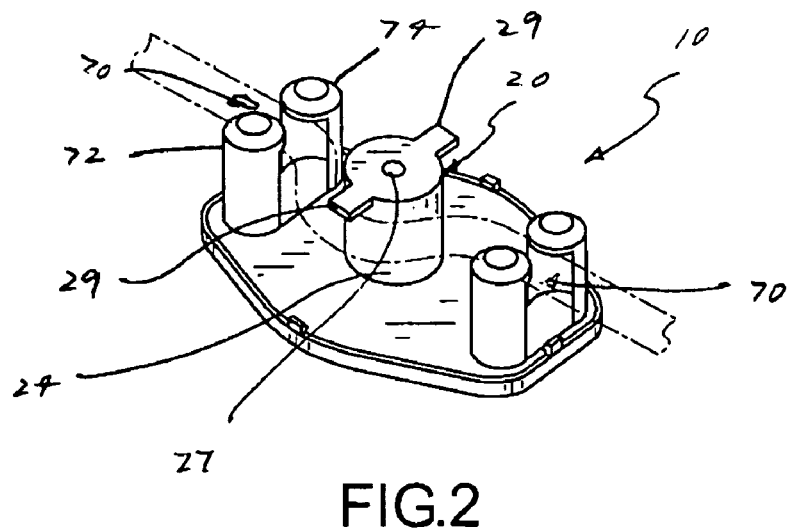

Referring now to FIGS. 1 and 3, a number of features may be noted that facilitate docking of a medical-liquid, male connector. First, the planar surface portion 32 of film member 30 and the surrounding, ring-shaped, conical surface portion 34 may be provided to be visually distinct from each other, as well as visually distinct from a top surface 46 of the flange member 40. That is, all or adjacent ones of the planar surface portion 32, ring-shaped, conical surface portion 34 and top surface 46 may be of a different hue or color so as to present a target-like appearance to a user. Further, directional indicia 48 may be provided on the top surface 46 of the flange member 40 so as to facilitate interconnection of the docking apparatus 10 and a medical-liquid, male connector. For example, directional arrows may be presented in a visually distinct manner to indicate the rotational direction that a collar of a medical-liquid, male connector should be turned (e.g. clockwise) relative to docking apparatus 10 in order to achieve a threaded interconnection therebetween.

To further facilitate the use of docking apparatus 10, holding member 20 may be provided with a reduced passageway 27 at the bottom end of the tubular portion 24. Such reduced passageway allows air and liquid to exit from within the holding member 20, yet restricts a user from attempting to dock a medical-liquid, male connector at the wrong end of tubular portion 24.

As illustrated by FIGS. 1, 2, and 4-6, docking apparatus 10 may include a number of slots 70 that are sized and located to selectively receive a medical liquid tubing line, (shown in phantom). For example, slots 70 may be provided between legs 72, 74 that extend away from the laterally-extending portion 26 at opposing ends of the docking apparatus 10. In this regard, each pair of legs 72, 74 may be spaced a distance that is slightly less than the diameter of a typical medical liquid tubing line used in a patient care facility (e.g. about 1/16-3/16") so as to facilitate, retentive engagement of the docking apparatus 10 relative to such tubing line. Further, by routing a tubing line between slots 70 and about the outside of the tubular portion 24 of the holding member 20, a tortuous path is defined, thereby further enhancing retentive placement. Retentive engagement of docking apparatus 10 with a tubular line is even further enhanced by the provision of sideward extending tabs 29 at a bottom end of tubular member 24 of the holding member 20.

Figure 7A:
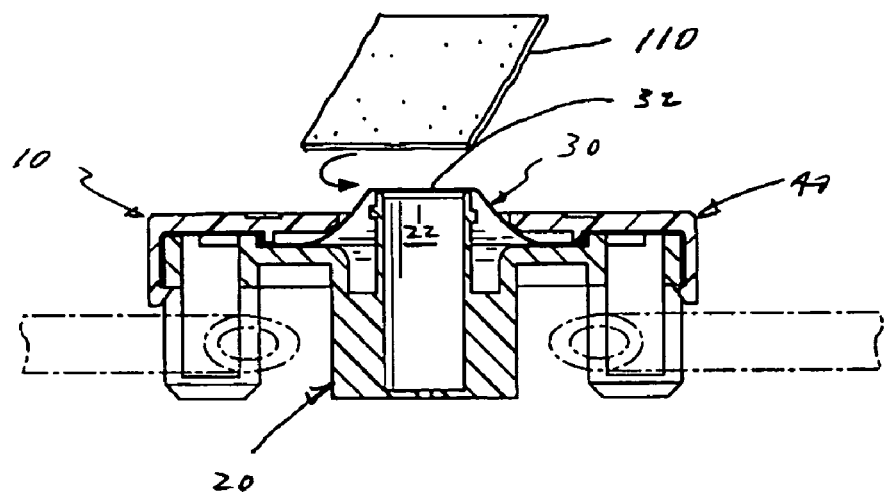
FIGS. 7A, 7B, 7C, 7D and 7E are side, cross-sectional views illustrating the use of the docking apparatus embodiment of FIGS. 1-6 with an exemplary medical-liquid, male connector.
Figure 7B:
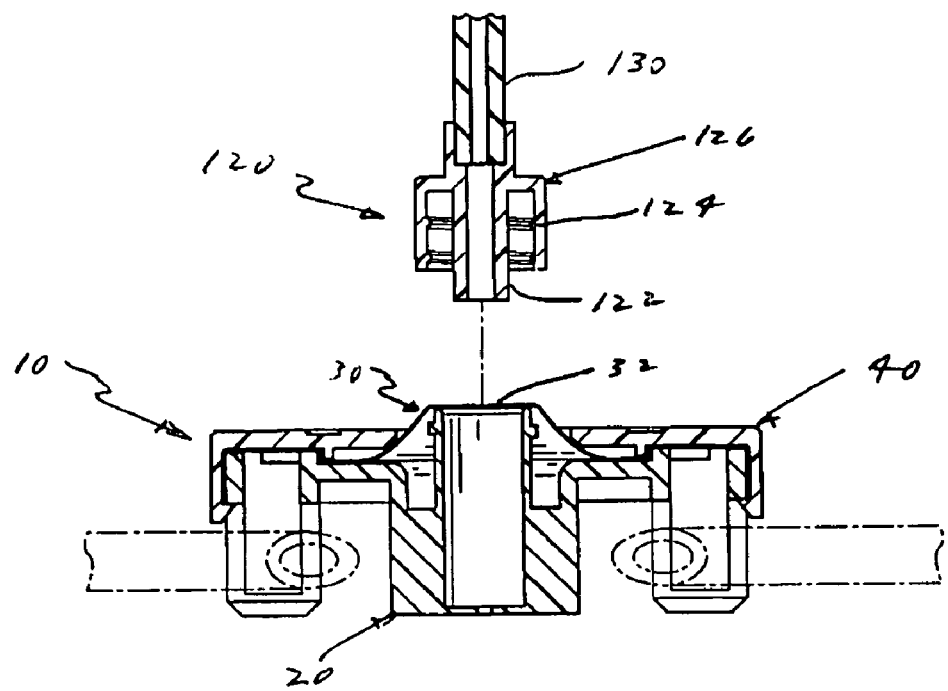

FIGS. 7A-7E illustrate an exemplary use of docking apparatus 10. As shown in each of the figures, the docking apparatus 10 may be interconnected to an exemplary tubing line (shown in phantom) prior to, during or after use of the docking apparatus. As illustrated by FIG. 7A, prior to docking an anti-bacterial material may be applied to the frusto-conical surface of the film member 30 using a swab 110. Then, as shown FIG. 7B, an exemplary medical-liquid, male connector 120, that is interconnected or interconnectable via a tubing line 130 with a medical liquid source, may be located in an aligned position with the opening 20 of docking apparatus 10. In this regard, and as noted above, a nozzle end 122 of the medical-liquid, male connector 120 may be visually aligned with the visibly distinct, planar surface portion 32 of film member 30. To initiate docking, the medical-liquid, male-connector 120 and/or docking apparatus 10 may be advanced so that the distal of nozzle end 122 of the medical-liquid, male connector 120 engages the planar surface portion 32 and the anti-bacterial material applied thereto.

Figure 7C:
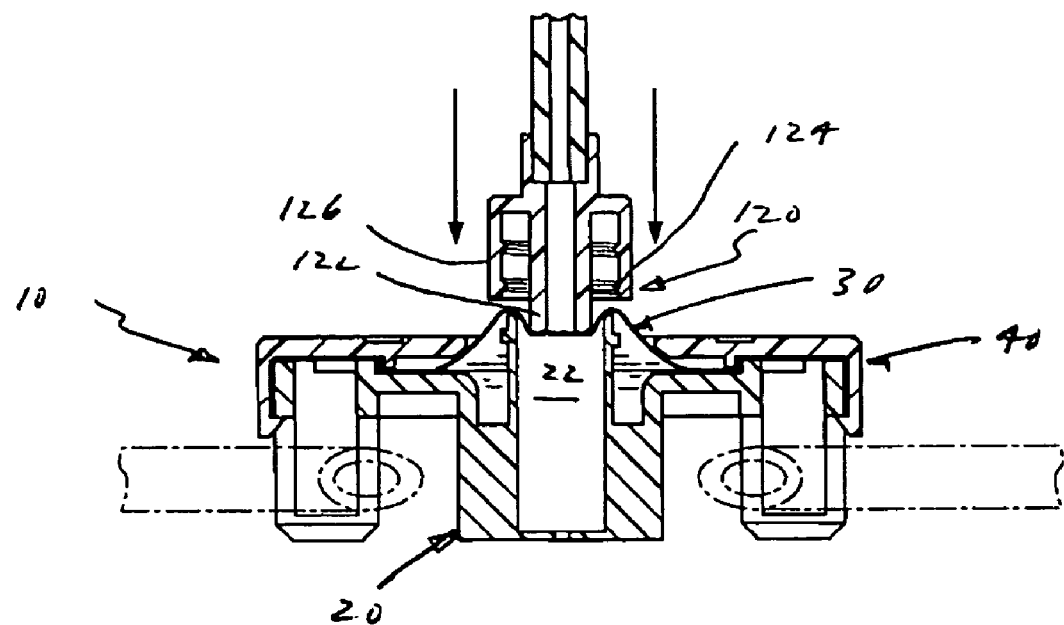

In FIG. 7C, as the nozzle end 122 of the medical-liquid, male connector 120 has engaged the planar surface portion 32 of the film member 30 and begun to stretch the film member 30 into the top end of the tubular portion 24 of the holding member 20. In this regard, it should be noted that during this first stage of stretching, the film member 30 advantageously stretches across an area whose periphery is defined by the interface of annular ring 27 on holding member 20 and annular ring 44 on flange member 40. Such an arrangement facilitates repeated use of the docking apparatus 10 by reducing the likelihood of elastic deformation of film member 30.

Figure 7D:
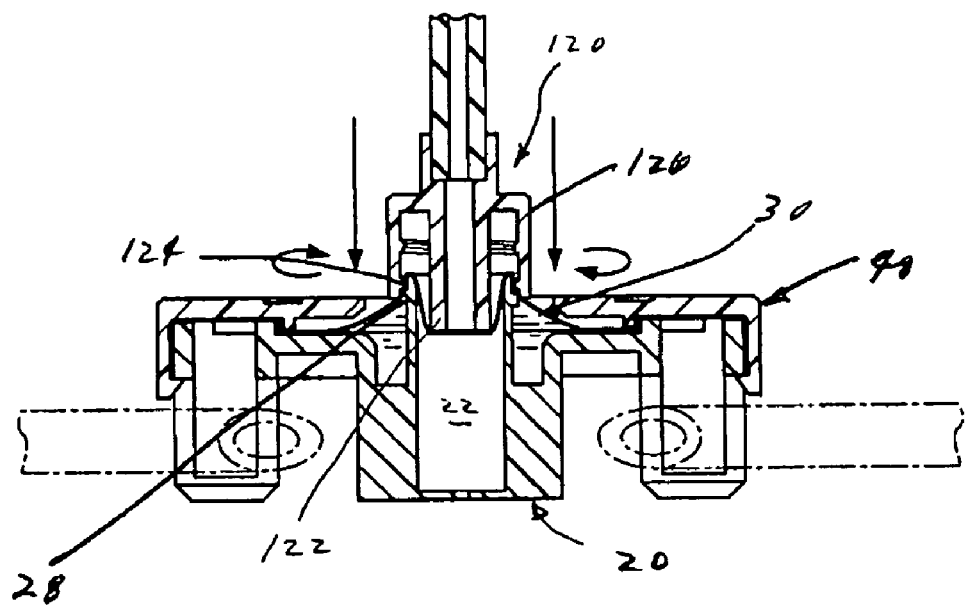

In FIG. 7D, the docking apparatus 10 and/or medical-liquid, male connector 120 has been further advanced, wherein film member 30 has been further stretched inward into the tubular member 20. Of note, threaded interconnection surface 124 on the inside surface of collar 126 of the medical-liquid, male connector 120 has interfaced with the threaded interconnection surface 28 provided on tubular portion 24 of the holding member 20. As such, upon relative rotation the two interconnection surfaces will restrainably engage the film member 30 therebetween. In turn, further stretching of film member 30 during a second stage will be substantially limited to the area of film member 30 that is located within the restricted region.

Figure 7E:
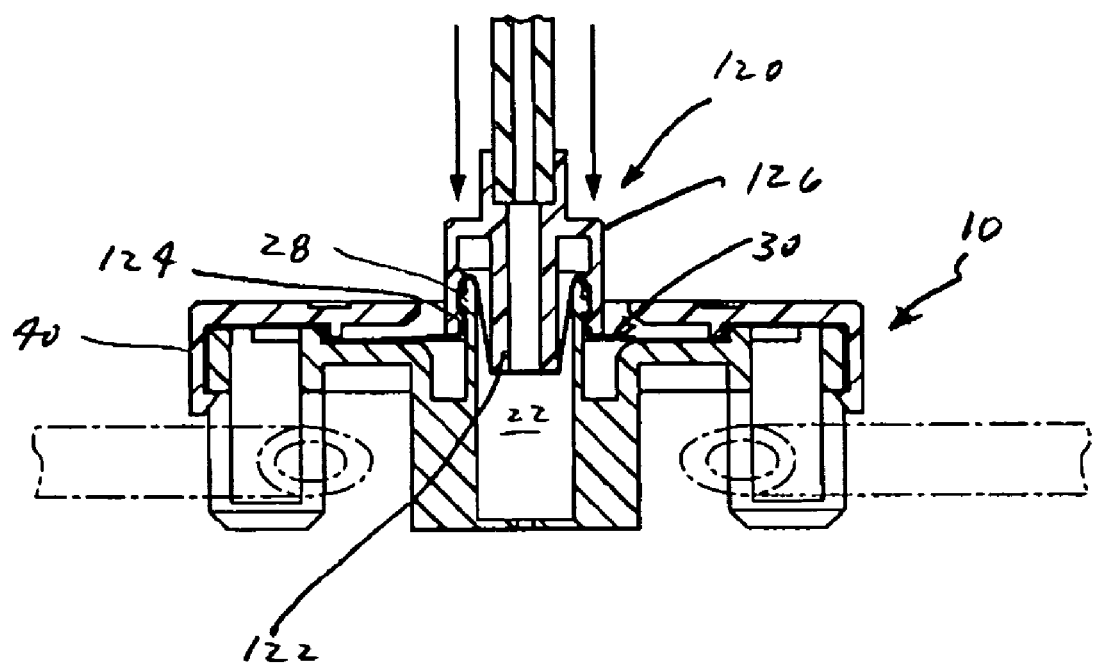

As shown in FIG. 7E, the collar 126 of the medical liquid, male-connector 120 has been rotated relative to the docking apparatus 10 so as to yield threaded engagement and relative advancement. Concomitantly, the nozzle end 122 of the medical liquid, male-connector 120 has been further advanced into the tubular portion 24 of the holding member 20, thereby further stretching film member 30. As may be appreciated, the medical-liquid, male connector 120 may be maintained in the docking position shown in FIG. 7E, wherein maintenance of the sterility of nozzle end 122 and the inside surface of collar 126 is enhanced. Subsequently, the medical-liquid male connector 120 may be disconnected from docking apparatus 10 by rotating collar 126, wherein film member may elastically return to substantially the same configuration shown in FIG. 7A. Thereafter, the docking apparatus 10 may be repeatedly used as described in relation to FIGS. 7A-7E over an extended period of patient treatment.

FIGS. 8A-8E illustrate another embodiment of a docking apparatus 100, as employed in conjunction with another medical-liquid, male connector 220. The docking apparatus 100 is of the same configuration as docking apparatus 10 illustrated in FIGS. 1-6 and 7A-7E, with the exception that it comprises an interconnection surface 102 that is located on the inside of tubular portion 24, as opposed to an interconnection surface on the outside of the tubular portion 24 as per the prior embodiment. Relatedly, the medical-liquid, male connector 220 is of the same configuration as the medical-liquid, male connector 120 illustrated in FIGS. 7B-7E, with the exception that medical-liquid, male connector 220 does not include an outer collar as per the prior embodiment. Further, the nozzle end 122 of the medical-liquid, male connector 220 includes an outer interconnection surface 224.

As will be appreciated, the interconnection surface 102 of docking apparatus 100 and interconnection surface 224 of medical-liquid, male connector 220 are sized and shaped for retentive interconnection. More particularly, in the illustrated arrangement, the interconnection surfaces 102 and 224 comprise complimentary threaded surfaces. In other arrangements, interconnection surface 224 could be modified to be a tapered outer surface on nozzle end 122 and interconnection surface 102 could be modified to be of a size/shape to slidably receive the tapered outer surface on nozzle end 122 so as to yield a friction-fit interface with film member 30 interposed therebetween.

Figure 8A:
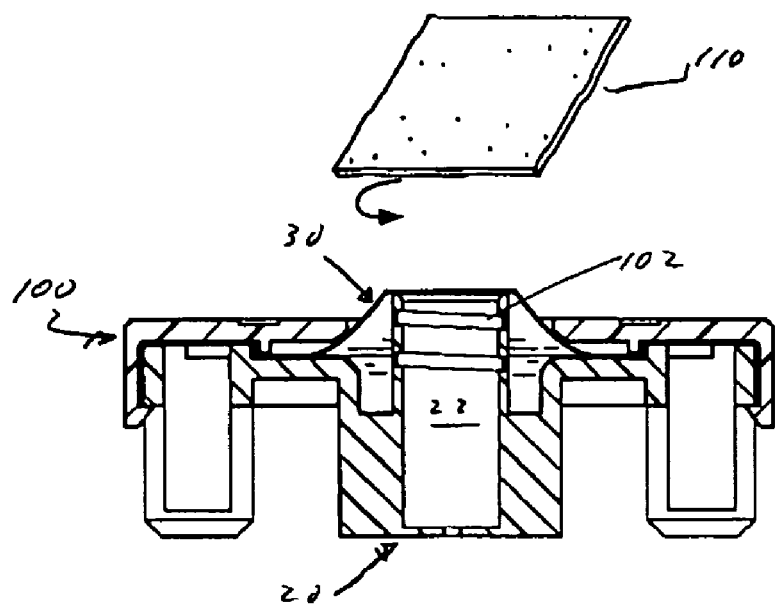
FIGS. 8A, 8B, 8C, 8D, and 8E are side, cross-sectional views illustrating the use of another docking apparatus embodiment with another medical-liquid, male connector.
Figure 8B:
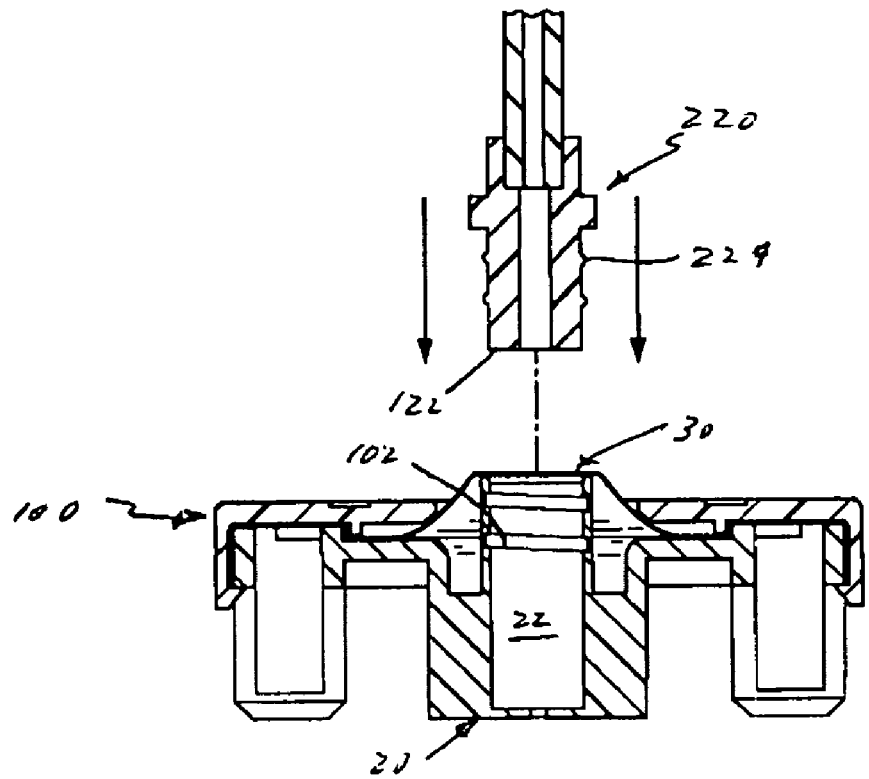

As illustrated by FIG. 8A, prior to docking an anti-bacterial material may be applied to the frusto-conical surface of the film member 30 using a swab 10. Then, as shown in FIG. 8B, a medical-liquid, male connector 220, interconnected or interconnectable via tubing line 130 with a medical liquid source, may be located in an aligned position with the opening 22 of docking apparatus 100. Again, nozzle end 122 of the medical-liquid, male connector 220 may be visually aligned in co-axial relation with the visibly distinct, planar surface portion 32 of the film member 30. To initiate docking, the medical-liquid, male connector 220 and/or docking apparatus 100 may be advanced so that the distal edge of the nozzle end 122 of the medical-liquid, male connector 220 engages the planar surface portion 32 and the anti-bacterial material applied thereto.

Figure 8C:
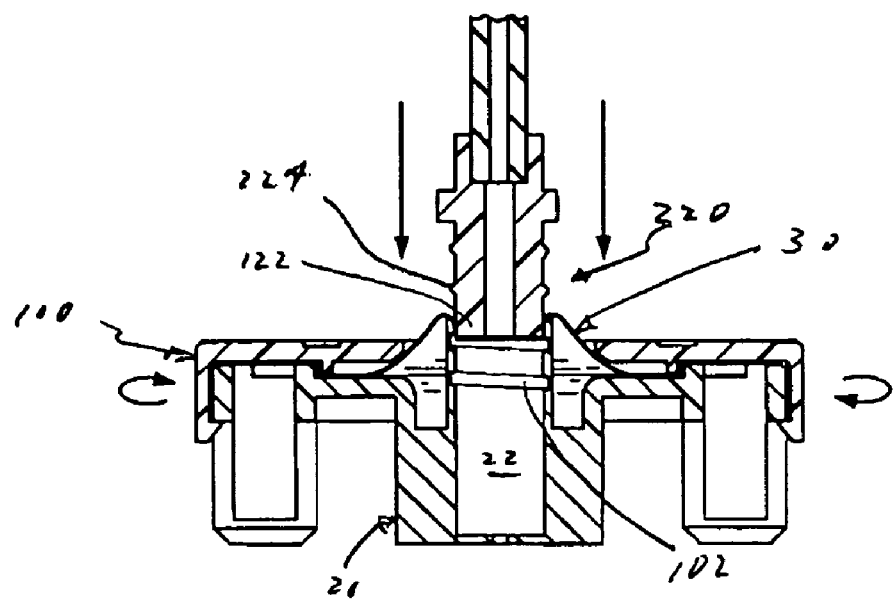

In FIG. 8C, the nozzle end 122 of the medical-liquid, male connector 220 has engaged the planar surface portion 32 of the film member 30 and begun to stretch the film member 30 into the top end of the tubular portion 24 of the holding member 20. Again, it should be noted that during this first stage of stretching the film member 30 advantageously stretches across an area that is greater than the size of the opening 22 of the tubular portion 24 of the holding member 20.

Figure 8D:
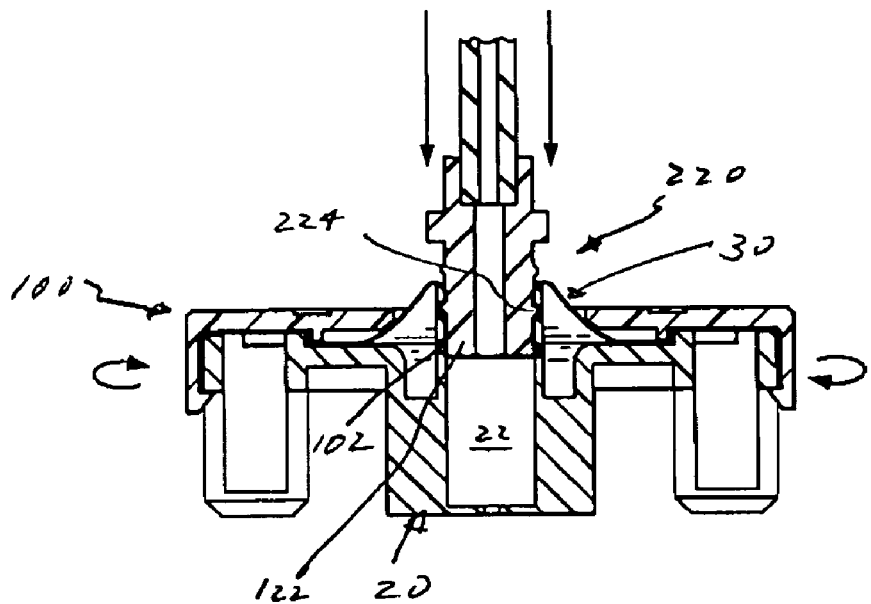

In FIG. 8D, the docking apparatus 100 and/or medical-liquid, male connector 220 has been further advanced. As shown, the threaded interconnection surface 224 on the outside of the nozzle end 122 of the medical-liquid, male connector 220 has begun to interface with the threaded interconnection surface 102 provided on the inside of tubular portion 24 of the holding member 20. As such, upon rotation of the docking apparatus 100 relative to medical-liquid, male connector 220, further stretching of the film member 30 during a second stage will be substantially limited to the area of the film member 30 that is located within the restrained region.

Figure 8E:
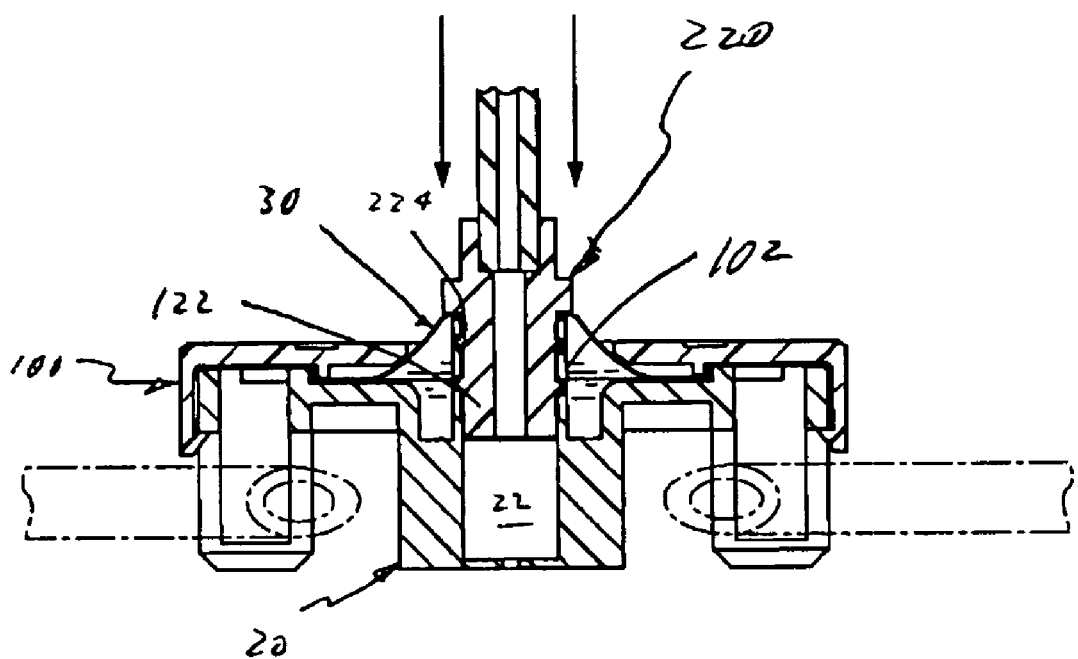

As shown in FIG. 8E, the docking apparatus 100 has been rotated relative to the medical-liquid, male connector 220 so as to yield threaded, retentive engagement. Concomitantly, the nozzle end 122 of the medical-liquid, male connector 220 has been further advanced into the tubular portion 24 of the holding member 20, thereby further stretching film member 30. The medical-liquid, male connector 220 may be maintained in the docking position shown in 8E, wherein maintenance of the sterility of nozzle end 122 and the interconnection surface 224 of nozzle end 122 is enhanced. Subsequently, the medical-liquid, male connector may be disconnected from docking apparatus 100 by rotating during apparatus 100, wherein film member 30 may elastically return to substantially the same configuration shown in FIG. 8A. Thereafter, the docking apparatus 100 may be repeatedly used as described in relation to FIGS. 8A-8E.

The embodiments discussed above are not intended to limit the scope of the present invention and various modifications, adaptations, and extensions of the present invention will be apparent to those skilled in the art. Such further embodiments are all intended to be encompassed by the scope of the present invention as characterized by the claims that follow.

What is claimed is:

1. A medical-liquid, male connector docking apparatus, comprising:
    a holding member having an opening for matably receiving a nozzle end of a male connector therethrough and a tubular portion, wherein a threaded surface is located on the outside of the tubular portion for receiving a complimentary threaded surface of a collar of a medical-liquid, male connector having a nozzle end insertable through said opening; and,
    a film member disposed across said opening, wherein said film member defines a continuous, outer surface portion across said opening prior to insertion of a nozzle end of a medical-liquid, male connector through said opening of the holding member, and wherein said film member is stretchable so that upon engagement by and relative advancement of a nozzle end of a medical-liquid, male connector inserted through said opening of the holding member the film member stretches to envelop in a tent-like manner and thereby isolate and maintain sterility of the nozzle end of the male connector.

2. A medical-liquid, male connector docking apparatus as recited in claim 1, wherein said film member is elongatable at least about 400%.

3. A medical-liquid, male connector docking apparatus as recited in claim 1, wherein said film member extends over said opening in co-planar relation to a periphery of said opening prior to insertion of a nozzle end of a medical-liquid, male connector through said opening.

4. A medical-liquid, male connector docking apparatus as recited in claim 1, wherein said film member is elastic.

5. A medical-liquid, male connector docking apparatus as recited in claim 4, wherein said elastic film member has a modulus of elasticity of at least about 1000 psi.

6. A medical-liquid, male connector docking apparatus as recited in claim 4, wherein said elastic film member comprises a polymer-based material.

7. A medical-liquid, male connector docking apparatus as recited in claim 1, wherein said tubular portion of said holding member comprises:
    an interconnection surface adapted for selective interconnection with a complimentary interconnection surface provided on a medical-liquid, male connector.

8. A medical-liquid, male connector docking apparatus as recited in claim 1, wherein said opening is located at a top end of said tubular portion.

9. A medical-liquid, male connector docking apparatus as recited in claim 8, wherein said film member extends outwardly from and about said top end of said tubular portion.

10. A medical-liquid, male connector docking apparatus as recited in claim 9, wherein said film member defines a continuous, ring-shaped surface portion surrounding said outer surface portion.

11. A medical-liquid, male connector docking apparatus as recited in claim 10, further comprising:
    a flange member interconnected to said holding member and extending laterally away from said tubular portion, wherein at least a portion of said tubular portion and at least a portion of said ring-shaped surface portion of the film member each project through and away from an aperture provided through said flange member.

12. A medical-liquid, male connector docking apparatus as recited in claim 11, wherein said holding member further includes:
    a laterally-extending portion interconnected to and extending laterally away from tubular portion, wherein said laterally-extending portion and said flange member are adapted for interconnection with a peripheral ring portion of said film member captured therebetween.

13. A medical-liquid, male connector docking apparatus as recited in claim 10, wherein said surface portion and said surrounding, ring-shaped surface portion are visually distinct.

14. A medical-liquid, male connector docking apparatus as recited in claim 1, wherein a portion of an outer surface of said film member is coaxially aligned with said opening and presented in a visually distinct manner.

15. A medical-liquid, male connector docking apparatus as recited in claim 14, wherein said portion of said outer surface of said film member corresponds in shape with said opening of said holding member.

16. A medical-liquid, male connector docking apparatus as recited in claim 1, wherein said film member comprises an anti-microbial material.

17. A medical-liquid, male connector docking apparatus as recited in claim 1, wherein said film member is disposed so that it is locatable in contact engagement with and between the threaded surface and a complimenting threaded surface of a medical-liquid, male connector upon said selective interconnection.

18. A medical-liquid, male connector docking apparatus as recited in claim 17, wherein said film member extends across and laterally away from said opening.

19. A method for docking a medical-liquid, male connector, comprising:
engaging a nozzle end of a medical-liquid, male connector with a surface of an outer film member disposed across an opening of a holding member comprising a docking apparatus by advancing at least one of said medical-liquid, male connector and said docking apparatus toward the other;
stretching said film member of said docking apparatus to envelop in a tent-like manner and thereby isolate and maintain sterility of said nozzle end of said medical-liquid, male connector by advancing at least one of said medical-liquid, male connector and said docking apparatus toward the other so that said nozzle end engages and stretches the film member as the nozzle end is inserted through said opening of the holding member of the docking apparatus; and,
interconnecting said medical-liquid, male connector with said docking apparatus by rotatably advancing a threaded interconnection surface on a collar of the medical-liquid, male connector relative to a threaded interconnection surface on a tubular portion of said holding member of the docking apparatus, wherein said nozzle end of the medical-liquid, male connector is maintained in said enveloped position.

20. A method as recited in claim 19, further comprising:
contacting said outer surface of said film member of the docking apparatus with an anti-bacterial material prior to said engaging and stretching steps.

21. A method as recited in claim 20, wherein a distal aspect of said nozzle end of the medical-liquid, male connector is maintained in contact engagement with said outer surface of the film member of the docking apparatus throughout said interconnecting step.

22. A method as recited in claim 20, wherein said film member is interposed between and in contact relation with said interconnection surface of the holding member of the docking apparatus and the complimentary interconnection surface of the medical-liquid, male connector throughout said interfacing step.

23. A method as recited in claim 19, wherein said stretching step includes:
first stretching said film member across a first area thereof that is larger than an area of said opening; and,
second stretching said film member across second area that is smaller than said first area.

24. A method as recited in claim 19, further comprising:
disconnecting said medical-liquid, male connector from said docking apparatus; and,
disengaging said nozzle end of the medical-liquid, male connector from said surface of the film member of the docking apparatus, wherein said surface of said film member elastically returns to an initial position.

25. A method as recited in claim 24, further comprising:
repeating said engaging, stretching, interconnecting, disconnecting, and disengaging steps in plurality of times.

26. A method as recited in claim 19, further comprising:
providing a portion of said outer surface of said film member in coaxial alignment with said opening of the holding member, wherein said portion is presented in a visually distinct manner.

27. A method as recited in claim 26, wherein said visually distinct portion of said outer surface of the film member corresponds in shape with said opening of the holding member comprising the docking apparatus.

* * * * *

UNITED STATES PATENT AND TRADEMARK OFFICE
CERTIFICATE OF CORRECTION

PATENT NO. : 7,611,505 B2  Page 1 of 1
APPLICATION NO. : 11/125774
DATED : November 3, 2009
INVENTOR(S) : Ranalletta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1153 days.

Signed and Sealed this

Twelfth Day of October, 2010

David J. Kappos
*Director of the United States Patent and Trademark Office*